(12) United States Patent
Zeyss et al.

(10) Patent No.: US 6,906,221 B2
(45) Date of Patent: Jun. 14, 2005

(54) METHOD FOR PRODUCING ACETIC ACID (75) Inventors: Sabine Zeyss, Konigstein (DE); Uwe Dingerdissen, Seeheim-Jugenheim (DE); Manfred Baerns, Berlin (DE); Dorit Wolf, Frankfurt (DE); David Linke, Berlin (DE)

(73) Assignee: Celanese International Corporation, Dallas, TX (US)

( * ) Notice: Subject to any disclaimer, the term of this patent is extended or adjusted under 35 U.S.C. 154(b) by 115 days.

(21) Appl. No.: 10/398,815

(22) PCT Filed: Oct. 17, 2001

(86) PCT No.: PCT/EP01/12001

§ 371 (c)(1),
(2), (4) Date: Aug. 12, 2003

(87) PCT Pub. No.: WO02/38526

PCT Pub. Date: May 16, 2002

(65) Prior Publication Data

US 2004/0133039 A1 Jul. 8, 2004

(30) Foreign Application Priority Data

Nov. 10, 2000 (DE) .......................................... 100 55 810

(51) Int. Cl.$^7$ .......................... C07C 51/14; C07C 51/16
(52) U.S. Cl. ....................................... 562/522; 562/548
(58) Field of Search ................................. 562/522, 548

(56) References Cited

U.S. PATENT DOCUMENTS 6,194,610 B1 * 2/2001 Borchert et al. ............ 562/548

FOREIGN PATENT DOCUMENTS

| DE | 19620542 | 11/1997 |
| DE | 19630832 | 2/1998 |
| WO | 8804199 | 6/1988 |
| WO | 0014047 | 3/2000 |

\* cited by examiner

Primary Examiner—Paul A. Zucker
(74) Attorney, Agent, or Firm—Muserlian, Lucas and Mercanti (57) ABSTRACT The invention relates to a method for producing acetic acid by oxidizing ethane in fluid bed reactors with high selectivity and high yields.

13 Claims, 6 Drawing Sheets

Fig. 1a

| j | Reaction | Rate equation | Rate constant at 539 K | $E_a$ or $\Delta H_{ads}$ |
|---|---|---|---|---|
| | *Ethane activation (Formation of adsorbed ethylene)* | | | |
| 1 | $C_2H_6 + Z\text{-}O \longrightarrow Z\text{-}C_2H_4 + H_2O$ | $r_1 = k_1\, p_{C2H6}\, \theta_{Z\text{-}O}$ | $k_1 = 1.665\cdot 10^{-9}$ mol (s kg Pa)$^{-1}$ | 99.7 kJ·mol$^{-1}$ |
| | *Acetic acid formation* | | | |
| 2 | $Z\text{-}C_2H_4 + O_2 \longrightarrow Z + CH_3COOH$ | $r_2 = k_2\, p_{O2}\, \theta_{Z\text{-}C2H4}$ | $k_2 = 1.251\cdot 10^{-9}$ mol (s kg Pa)$^{-1}$ | 92.6 kJ·mol$^{-1}$ |
| 3 | $C_2H_4 + X\text{-}OHOH + 0.5\, O_2 \longrightarrow CH_3COOH + X + H_2O$ | $r_3 = k_3\, p_{C2H4}\, \theta_{X\text{-}OHOH}$ | $k_3 = 1.254\cdot 10^{-5}$ mol (s kg Pa)$^{-1}$ | 144 kJ·mol$^{-1}$ |
| | *Reoxidation of the catalyst* | | | |
| 4 | $0.5\, O_2 + Z \longrightarrow Z\text{-}O$ | $r_4 = k_4\, p_{O2}\, \theta_Z$ | $k_4 = 1.713\cdot 10^{-8}$ mol (s kg Pa)$^{-1}$ | −123 kJ·mol$^{-1}$ |
| 5 | $0.5\, O_2 + X \longrightarrow X\text{-}O$ | $r_5 = k_5\, p_{O2}\, \theta_X$ | $k_5 = 4.453\cdot 10^{-9}$ mol (s kg Pa)$^{-1}$ | 85.2 kJ·mol$^{-1}$ |
| | *Adsorption/desorption of ethylene and water* | | | |
| 6 | $C_2H_4 + Z \rightleftharpoons Z\text{-}C_2H_4$ | $r_6 = k_6\, p_{C2H4}\, \theta_Z - k_6/K_6\, \theta_{Z\text{-}C2H4}$ | $k_6 = 6.633\cdot 10^{-8}$ mol (s kg Pa)$^{-1}$ $K_6 = 2.484\cdot 10^{-4}$ Pa$^{-1}$ | −137 kJ·mol$^{-1}$ −176 kJ·mol$^{-1}$ |
| 7 | $H_2O + Z \rightleftharpoons Z\text{-}OH_2$ | $r_7 = k_7\, p_{H2O}\, \theta_Z - k_7/K_7\, \theta_{Z\text{-}OH2}$ | $K_7 = 1.359\cdot 10^{-7}$ Pa$^{-1}$ | −220 kJ·mol$^{-1}$ |
| | *Formation of the Wacker-like centre* | | | |
| 8 | $X\text{-}O + H_2O \rightleftharpoons X\text{-}OHOH$ | $r_8 = k_8\, p_{H2O}\, \theta_{X\text{-}O} - k_8/K_8\, \theta_{X\text{-}OHOH}$ | $k_8 = 2.634\cdot 10^{-9}$ mol (s kg Pa)$^{-1}$ $K_8 = 5.396\cdot 10^{-6}$ Pa$^{-1}$ | −25.7 kJ·mol$^{-1}$ −38.8 kJ·mol$^{-1}$ |
| | *Non selective reaction steps* | | | |
| 9 | $C_2H_6 + Z\text{-}O + 3\, O_2 \longrightarrow [\,^*\,] \longrightarrow 2\, CO_2 + 3\, H_2O + Z$ | $r_9 = k_9\, p_{C2H6}\, \theta_{Z\text{-}O}$ | $k_9 = 3.363\cdot 10^{-10}$ mol (s kg Pa)$^{-1}$ | 123 kJ·mol$^{-1}$ |
| 10 | $C_2H_4 + Z\text{-}O + 2.5\, O_2 \longrightarrow [\,^*\,] \longrightarrow 2\, CO_2 + 2\, H_2O + Z$ | $r_{10} = k_{10}\, p_{C2H4}\, \theta_{Z\text{-}O}$ | $k_{10} = 2.019\cdot 10^{-8}$ mol (s kg Pa)$^{-1}$ | 43.3 kJ·mol$^{-1}$ |
| 11 | $CH_3COOH + Z\text{-}O + 1.5\, O_2 \longrightarrow [\,^*\,] \longrightarrow 2\, CO_2 + 2\, H_2O + Z$ | $r_{11} = k_{11}\, p_{HOac}\, \theta_{Z\text{-}O}$ | $k_{11} = 2.892\cdot 10^{-9}$ mol (s kg Pa)$^{-1}$ | 105 kJ·mol$^{-1}$ |

Fig. 1b

| | |
|---|---|
| $\theta_{X-OHOH} =$ | $k_8\, p_{O2}\, p_{H2O} / (\, k_3\, p_{O2}\, p_{C2H4} + k_8\, p_{O2}\, p_{H2O} + k_3\, k_8/k_5\, p_{C2H4}\, p_{H2O} + k_8/K_8\, p_{O2}\,)$ |
| $\theta_{X-O} =$ | $(\, k_3\, p_{C2H4} + k_8/K_8\,)\, p_{O2} / (\, k_3\, p_{O2}\, p_{C2H4} + k_8\, p_{O2}\, p_{H2O} + k_3\, k_8/k_5\, p_{C2H4}\, p_{H2O} + k_8/K_8\, p_{O2}\,)$ |
| $\theta_X =$ | $1 - \theta_{X-OHOH} - \theta_{X-O}$ |
| $\theta_{Z-O} =$ | $k_4\, p_{O2}\, (k_2\, K_6\, p_{O2} + k_6) / [\, (k_2\, K_6\, p_{O2} + k_6)(k_1\, p_{C2H6} + k_9\, p_{C2H6} + k_{10}\, p_{C2H4} + k_{11}\, p_{HOac}) + K_7\, p_{H2O}\, (k_2\, K_6\, k_1\, p_{C2H6}\, p_{O2} + k_2\, K_6\, k_9\, p_{C2H6}\, p_{O2} + k_2\, K_6\, k_{10}\, p_{O2}\, p_{C2H4} + k_2\, K_6\, k_{11}\, p_{O2}\, p_{HOac} + k_6\, k_1\, p_{C2H6} + k_6\, k_9\, p_{C2H6} + k_6\, k_{10}\, p_{C2H4} + k_6\, k_{11}\, p_{HOac}) + K_6\, (k_4\, k_1\, p_{C2H6}\, p_{O2} + k_6\, k_1\, p_{C2H6}\, p_{C2H4} + k_6\, k_9\, p_{C2H6}\, p_{C2H4} + k_6\, k_{10}\, (p_{C2H4})^2 + k_6\, k_{11}\, p_{C2H4}\, p_{HOac}) + k_4\, p_{O2}\, (k_2\, K_6\, p_{O2} + k_6)\,]$ |
| $\theta_{Z-C2H4} =$ | $K_6\, (\, k_4\, k_1\, p_{C2H6}\, p_{O2} + k_6\, k_1\, p_{C2H6}\, p_{C2H4} + k_6\, k_9\, p_{C2H6}\, p_{C2H4} + k_6\, k_{10}\, (p_{C2H4})^2 + k_6\, k_{11}\, p_{C2H4}\, p_{HOac}\,) / [\, (k_2\, K_6\, p_{O2} + k_6)(k_1\, p_{C2H6} + k_9\, p_{C2H6} + k_{10}\, p_{C2H4} + k_{11}\, p_{HOac}) + K_7\, p_{H2O}\, (k_2\, K_6\, k_1\, p_{C2H6}\, p_{O2} + k_2\, K_6\, k_9\, p_{C2H6}\, p_{O2} + k_2\, K_6\, k_{10}\, p_{O2}\, p_{C2H4} + k_2\, K_6\, k_{11}\, p_{O2}\, p_{HOac} + k_6\, k_1\, p_{C2H6} + k_6\, k_9\, p_{C2H6} + k_6\, k_{10}\, p_{C2H4} + k_6\, k_{11}\, p_{HOac}) + K_6\, (k_4\, k_1\, p_{C2H6}\, p_{O2} + k_6\, k_1\, p_{C2H6}\, p_{C2H4} + k_6\, k_9\, p_{C2H6}\, p_{C2H4} + k_6\, k_{10}\, (p_{C2H4})^2 + k_6\, k_{11}\, p_{C2H4}\, p_{HOac}) + k_4\, p_{O2}\, (k_2\, K_6\, p_{O2} + k_6)\,]$ |
| $\theta_{Z-OH2} =$ | $K_7\, p_{H2O}\, (\, k_2\, K_6\, k_1\, p_{C2H6}\, p_{O2} + k_2\, K_6\, k_9\, p_{C2H6}\, p_{O2} + k_2\, K_6\, k_{10}\, p_{O2}\, p_{C2H4} + k_2\, K_6\, k_{11}\, p_{O2}\, p_{HOac} + k_6\, k_1\, p_{C2H6} + k_6\, k_9\, p_{C2H6} + k_6\, k_{10}\, p_{C2H4} + k_6\, k_{11}\, p_{HOac}\,) / [\, (k_2\, K_6\, p_{O2} + k_6)(k_1\, p_{C2H6} + k_9\, p_{C2H6} + k_{10}\, p_{C2H4} + k_{11}\, p_{HOac}) + K_7\, p_{H2O}\, (k_2\, K_6\, k_1\, p_{C2H6}\, p_{O2} + k_2\, K_6\, k_9\, p_{C2H6}\, p_{O2} + k_2\, K_6\, k_{10}\, p_{O2}\, p_{C2H4} + k_2\, K_6\, k_{11}\, p_{O2}\, p_{HOac} + k_6\, k_1\, p_{C2H6} + k_6\, k_9\, p_{C2H6} + k_6\, k_{10}\, p_{C2H4} + k_6\, k_{11}\, p_{HOac}) + K_6\, (k_4\, k_1\, p_{C2H6}\, p_{O2} + k_6\, k_1\, p_{C2H6}\, p_{C2H4} + k_6\, k_9\, p_{C2H6}\, p_{C2H4} + k_6\, k_{10}\, (p_{C2H4})^2 + k_6\, k_{11}\, p_{C2H4}\, p_{HOac}) + k_4\, p_{O2}\, (k_2\, K_6\, p_{O2} + k_6)\,]$ |
| $\theta_Z =$ | $1 - \theta_{Z-O} - \theta_{Z-C2H4} - \theta_{Z-OH2}$ |

METHOD FOR PRODUCING ACETIC ACID

This application is a 371 of PCT/EP01/12001 filed Oct. 17, 2001.

The invention relates to a process for preparing acetic acid by oxidation of ethane with high selectivity and in high yield in fluidized-bed reactors.

The catalytic gas-phase oxidation of ethane to ethylene and acetic acid has been known for a long time. The reaction is influenced essentially by the choice of reaction conditions; this is particularly true of the selectivity of the reaction. In general, acetic acid is formed only as by-product, while the main product is ethylene which may, under some circumstances, be oxidized further to carbon dioxide.

DE 196 30 832 A1, DE 196 20 542 A1, DE 197 45 902 A1, WO 98/47850 and WO 98/47851 describe a process for preparing acetic acid by partial oxidation of ethane using $MO_aPd_bX_cY_d$ as catalysts in a fixed bed. The catalyst has a high stability and a high selectivity in the oxidation of ethane to acetic acid. However, difficulties are presented in the process by the fact that the oxidation of ethane to acetic acid is strongly exothermic. Particularly in relatively large fixed-bed reactors, the heat of reaction can be removed only unsatisfactorily. This results in an increase in the temperature in the reactor and thus a reduction in the selectivity of the reaction.

To circumvent this problem, attempts have been made to carry out the reaction in a fluidized catalyst bed as described, for example, in U.S. Pat. No. 5,300,684, where cooling tubes are located directly in the fluidized-bed reactor to remove heat. A further development of the process is described in WO 00/14047. A disadvantage of the fluidized-bed process as described there has hitherto been that the oxidation of ethane to acetic acid still proceeds with a low selectivity and a lower space-time yield than in a fixed-bed reactor.

It is therefore an object of the present invention to provide a process for the oxidation of ethane to acetic acid in a fluidized-bed reactor which can be operated with higher selectivity and thus with a higher yield than the processes described hitherto.

In the present invention, it has surprisingly been able to be shown that the selectivity of the oxidation of ethane to acetic acid depends on the size of the gas bubbles in the fluidized catalyst bed. In particular, bubble sizes of <12 cm are advantageous. Particular preference is given to bubbles having a diameter of <5 cm.

At a given average particle size of the catalyst used, the size of the bubbles can be set by controlling the volume flow of gas. Bubble sizes of <12 cm can only be achieved by use of catalyst particles having a mean diameter of less than or equal to 80 μm.

The present invention accordingly provides a process for the direct catalytic oxidation of ethane to acetic acid in a fluidized bed comprising up to 70% of catalyst particles having a diameter of less than or equal to 80 μm. The fluidized bed preferably additionally contains smaller particles having a particle size of from 10 to 60 μm, and the distribution of the particle sizes should be such that 10–60% of the particles have a diameter of less than 60 μm. Particular preference is given to a distribution of the particle sizes such that catalyst particles are present in a diameter range of 10–40 μm. In a particularly preferred embodiment, the diameter of 20–50% of the catalyst particles is less than 40 μm.

The fluidized bed index to be set (the fluidized bed index is the ratio of gas velocity set to minimum fluidization velocity) has to be above 1. This means that the fluidized bed has to be in the fluid state. At a pressure of 16 bar and a temperature of 280° C., the minimum fluidization velocity at a particle diameter of 80 μm is 5.85 mm/s. The fluidized bed index is preferably in the range from 1 to 12.

As catalysts, it is possible to use all catalysts known to those skilled in the art. Catalysts which have been found to be advantageous are catalysts of the formula (I):

$$Mo_aPd_bX_cY_d \qquad (I)$$

where X is one or more elements selected from the group consisting of Cr, Mn, Nb, B, Ta, Ti, V, Te, W and Re and Y is one or more elements selected from the group consisting of B, Al, Ga, In, Pt, Zn, Cd, Bi, Ce, Co, Rh, Ir, Cu, Ag, Au, Fe, Ru, Cs, Mg, Ca, Sr, Ba, Li, K, Na, Rb, Be, Nb, Zr, Hf, Ni, P, Pb, Sb, Si, Sn, Tl and U.

The indices a, b, c and d are the gram atom ratios of the corresponding elements, where, based on a=1 b is in the range from 0.0001 to 0.01, preferably from 0.0001 to 0.001, c is in the range from 0.1 to 1 and d is in the range from 0 to 1.

X and/or Y may also represent a plurality of elements, in which case the indices c and d may assume different values for different elements.

The catalyst particularly preferably comprises at least one of the following compositions in combination with oxygen:

$Mo_{1.0}Pd_{0.0005}V_{0.25}Nb_{0.12}$ $Mo_{1.00}Pd_{0.0005}V_{0.45}Nb_{0.03}Sb_{0.01}Ca_{0.01}$ $Mo_{1.00}Pd_{0.0005}V_{0.45}Nb_{0.03}Sb_{0.01}Ca_{0.01}K_{0.015}$ $Mo_{1.00}Pd_{0.00075}V_{0.45}Nb_{0.03}Sb_{0.01}Ca_{0.01}$ $Mo_{1.00}Pd_{0.00075}V_{0.55}Nb_{0.03}Sb_{0.01}Ca_{0.01}$ $Mo_{1.00}Pd_{0.00075}V_{0.45}Nb_{0.06}Sb_{0.01}Ca_{0.01}$ $Mo_{1.00}Pd_{0.0008}V_{0.55}Nb_{0.06}Sb_{0.01}Ca_{0.01}$ $Mo_{1.00}Pd_{0.00085}V_{0.55}Nb_{0.06}Sb_{0.01}Ca_{0.01}$ $Mo_{1.00}Pd_{0.00075}V_{0.55}Nb_{0.09}Sb_{0.01}Ca_{0.01}$ $Mo_{1.00}Pd_{0.0008}V_{0.50}Nb_{0.15}Te_{0.01}Ca_{0.01}$ $Mo_{1.00}Pd_{0.00075}V_{0.50}Nb_{0.09}W_{0.01}Pd_{0.0003}$

Apart from the reaction gases ethane and oxygen, the reaction gas mixture may further comprise water vapor and inert gases such as nitrogen or carbon dioxide. It is also possible to employ a reaction gas composition above the explosive limit in the fluidized-bed reactor. However, the reactor is preferably operated using an excess of inert gas, water and/or ethane. Water vapor accelerates the oxidation of ethane to acetic acid at the expense of the oxidation of ethane to ethylene and thus results in an increase in the selectivity to acetic acid.

The process is preferably carried out at low temperatures. Low temperatures increase the selectivity of the oxidation reaction in favor of acetic acid. A temperature range of from 100 to 500° C. at a reactor pressure of from 1 to 50 bar is preferred.

The density of the catalyst particles can be in the range from 500 to 6000 kg/m³. To carry out the process, it is possible to use, for example, a fluidized-bed reactor as is described in U.S. Pat. No. 5,300,684.

The process of the invention has a high selectivity, and increased space-time yields can accordingly be achieved in the oxidation of ethane to acetic acid at moderate temperatures in a fluidized-bed reactor. Furthermore, reduction of the bubble size enables troublesome backmixing of the reactants in the fluidized bed to be reduced. This likewise leads to an increased selectivity of the reaction, resulting in an increase in the space-time yield of acetic acid.

BRIEF DESCRIPTION OF THE DRAWINGS

FIGS. 1a and 1b relate to the kinetic parameters determined for the reaction.

In a particular embodiment, especially when high ethane conversions are desired, the reaction can be carried out in a multistage fluidized-bed reactor with dedicated introduction of gas into each stage. Bubble growth commences afresh in each stage, so that the bubble size is on average smaller than in a single-stage fluidized bed. The small bubbles can also be achieved by means of internals, e.g. meshes, in the fluidized bed. To achieve high ethane conversions at the same time as a high selectivity to acetic acid, an additional divided introduction of oxygen into individual stages can be advantageous.

The advantageous bubble sizes in a fluidized bed and the corresponding reaction parameters were determined from measured results obtained in investigations of the catalytic gas-phase oxidation of ethane in a fixed bed. The kinetic parameters determined therefrom for the reactions involved are summarized in FIGS. 1a and 1b. The catalytic gas-phase oxidation of ethane is catalyzed by two different catalytically active sites Z and X on the catalyst. Z is a site where all oxidation steps occur, namely the oxidative dehydrogenation of ethane, the partial and complete oxidations of ethene and of acetic acid. X is a position on the catalyst which becomes active only in the presence of water. The activated form of X (X—OHOH) leads to conversion of ethene into acetic acid via a mechanism similar to the Wacker reaction. The formation of acetic acid thus proceeds via two different reaction paths—via the partial oxidation of ethene at the position Z (step 2 in FIG. 1a) and via a mechanism similar to the Wacker reaction at position X (step 3 in FIG. 1a). The necessary kinetic values to the intermediates at the catalytically active surface in the steady state, viz. Z, Z—$OH_2$, Z—O, Z—$CH_2H_4$, X—OHOH and X—O, were determined analytically and are given in table X.

The values determined in this way were used to simulate the fluidized-bed reactor according to the bubble assemblage model (BAM) (K. Kato, C. H. Wen, Chem. Eng. Sci. 24, 1351–1368 (1969)).

The model describes the fluidized bed as a two-phase system which consists of a bubble phase which is low in catalyst and a catalyst-rich emulsion phase; the two-phase structure of such a reaction mixture comprising particles in a fluidized bed with gas being passed through it can be verified with the naked eye. Since the emulsion phase contains a high proportion of solid, the catalytic reaction takes place there, while virtually no reaction takes place in the bubble phase owing to the low concentration of the catalytic material. The model of the fluidized-bed reactor therefore has to describe the transfer of reactants and products between the bubble phase and the emulsion phase and at the same time take account of the growth of the bubbles with increasing distance from the gas distributor, an effect which is well known from fluidized beds. For this reason, the fluidized bed was divided into segments with a height corresponding to the local bubble diameter. The bubble diameter, the velocity of the bubbles, the expansion of the bed and the local volume fractions of the phases were calculated by the methods of Werther (J. Werther, Chem. Eng. Sci. 47 (9–11), 2457–2462 (1992)) and Murray (J. D. Murray, J. Fluid. Mech. 21, 465 (1965)). For both bubble phase and emulsion phase, each segment was described as an ideal stirred tank. Owing to the good heat removal from fluidized-bed reactors, approximately isothermal reaction conditions can be achieved; for this reason, the reactor was regarded as isothermal for the purposes of modeling.

The mass equation for the two phases is given by the following equations:

Emulsion phase:

$$0 = A_{96} u_{mf} [c_{E,i,k-1} - c_{E,i,k}] + k_{BE,k} V_{B,k} [c_{B,i,k} - c_{E,i,k}] + \Sigma v_{i,j} r_{E,j,k} (1 - \epsilon_{mf}) \rho_{cat} V_{e,k} \quad \text{Eq. 1}$$

Bubble phase:

$$0 = A_{96} u_{mf} (u_k - u_{mf}) [c_{B,i,k-1} - c_{B,i,k}] - k_{BE,k} V_{B,k} [c_{B,i,k} - c_{E,i,k}] \quad \text{Eq. 2}$$

The equations can be solved for each reaction component i and each segment k, for example by means of the Wegstein method. The mass transfer between the bubble phase and the emulsion phase, which is expressed by the coefficient $K_{BE,i,k}$, can be determined quantitatively by means of a correlation of Sit and Grace (S. P., Sit, J. R. Grace, Chem. Eng. Sci. 36, 327–335 (1981)). The minimum fluidization velocity $u_{mf}$ is derived as described in Wen et al (C. Y. Wen, Y. H. Yu, AIChE J. 12, 610 (1966)).

The direct catalytic oxidation of ethane to acetic acid in a fluidized bed can be described to a good degree of accuracy by means of the model developed here.

The results are shown in FIGS. 2 to 7. $\tau_m$ in the figures and tables is the modified space-time given by the quotient of catalyst mass and volume flow under the respective reaction conditions.

Figure 2:
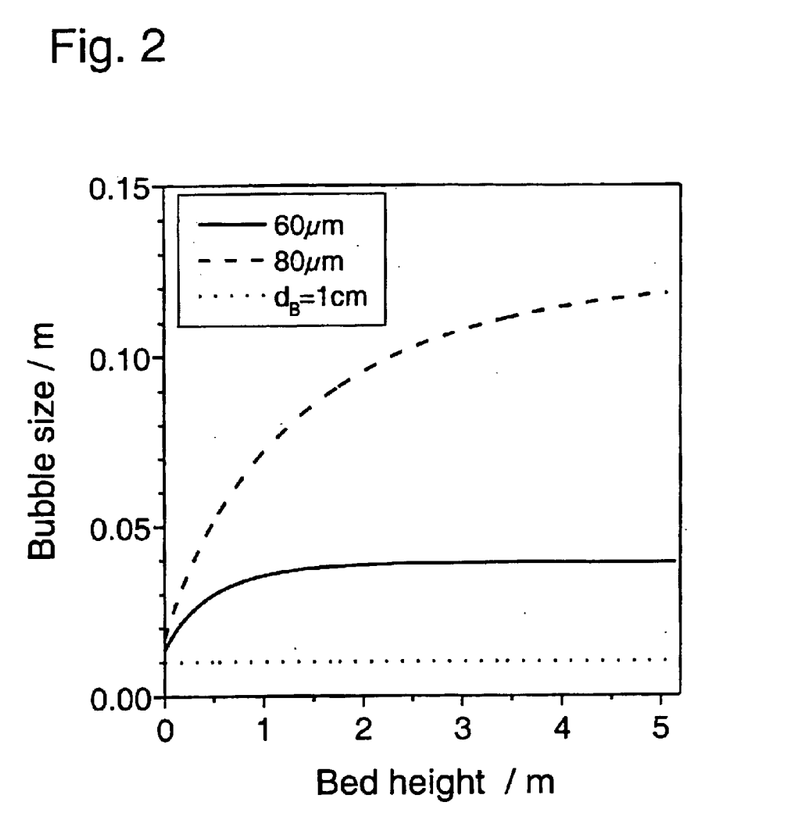
FIGS. 2 to 8 are graphs of the modified space-time given by the quotient of catalyst mass and volume flow under the reaction conditions.

FIG. 2 shows the bubble diameter as a function of the height above the gas feed point for different particle diameters of 60 $\mu$m and 80 $\mu$m.

Figure 3:
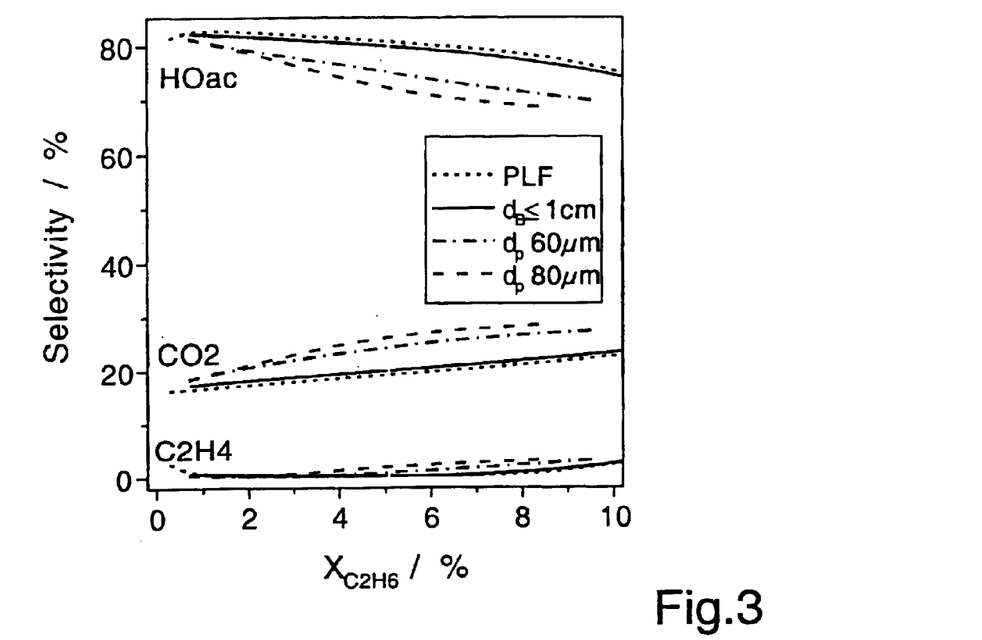
Figure 4:
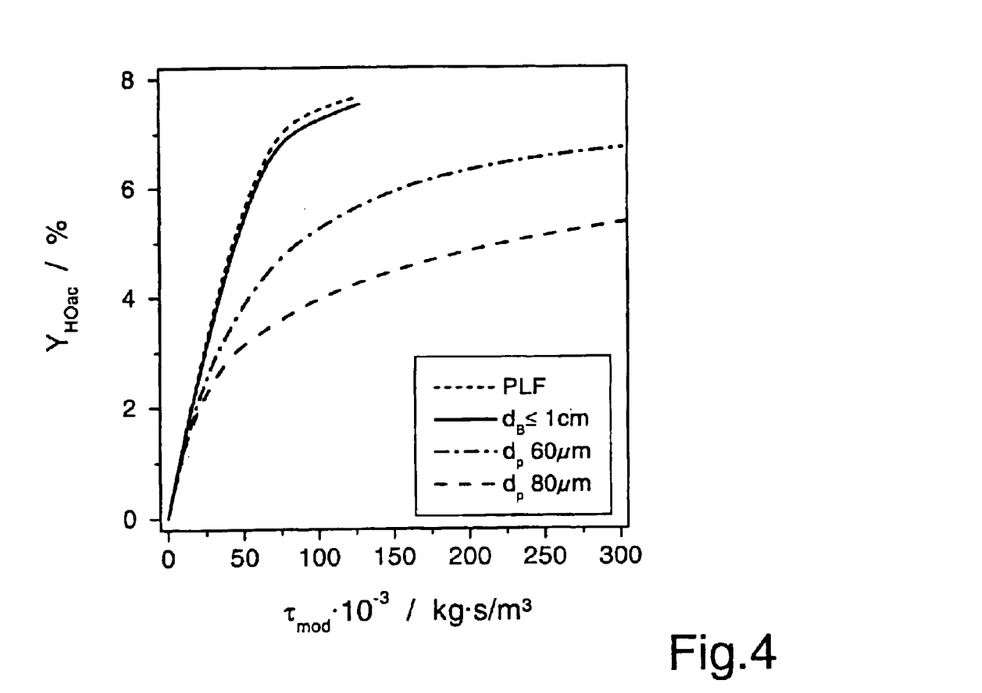

FIG. 3 shows the conversion selectivity curves and FIG. 4 shows the yield of acetic acid as a function of the residence time for various particle and bubble diameters under the following reaction conditions: T=260° C., $P_{tot}$=16 bar, feed composition $C_2H_6$:$O_2$:$H_2O$:$N_2$=40:8:20:32.

Figure 5:
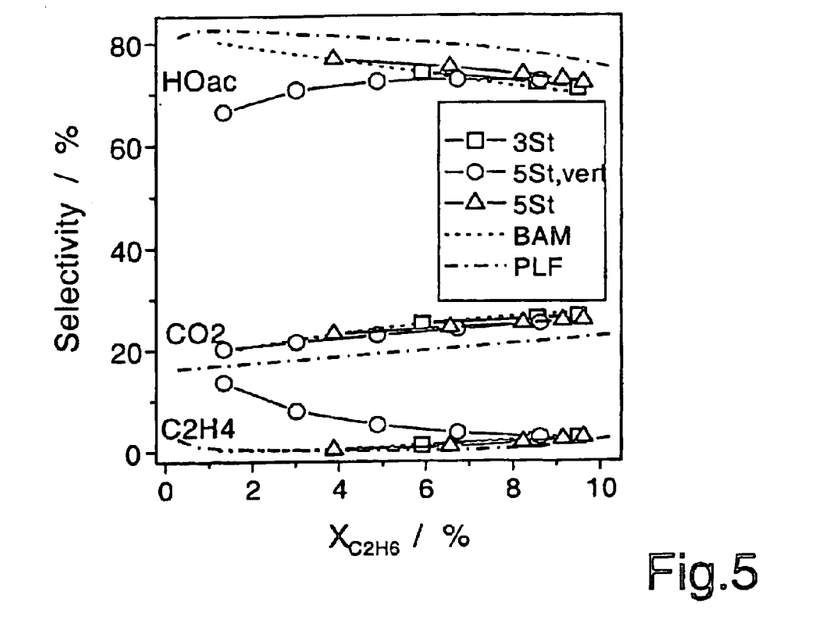
Figure 6:
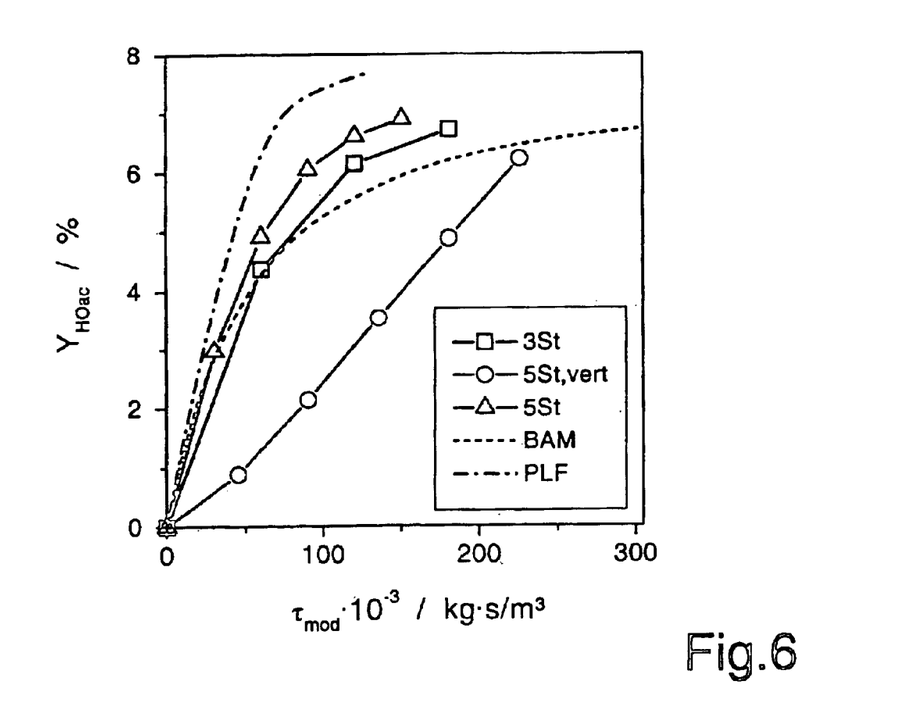

FIG. 5 shows the conversion selectivity curves and FIG. 6 the yield of acetic acid as a function of the residence time for multistage fluidized beds (see above); the points indicate the composition at the outlet of each stage (reaction conditions: T=260° C., $P_{tot}$=16 bar, $d_p$=60 $\mu$m, feed composition $C_2H_6$:$O_2$:$H_2O$: $N_2$=40:8:20:32 (in the case of divided introduction of oxygen in the first stage: 40:1.6:20:32)).

Figure 7:
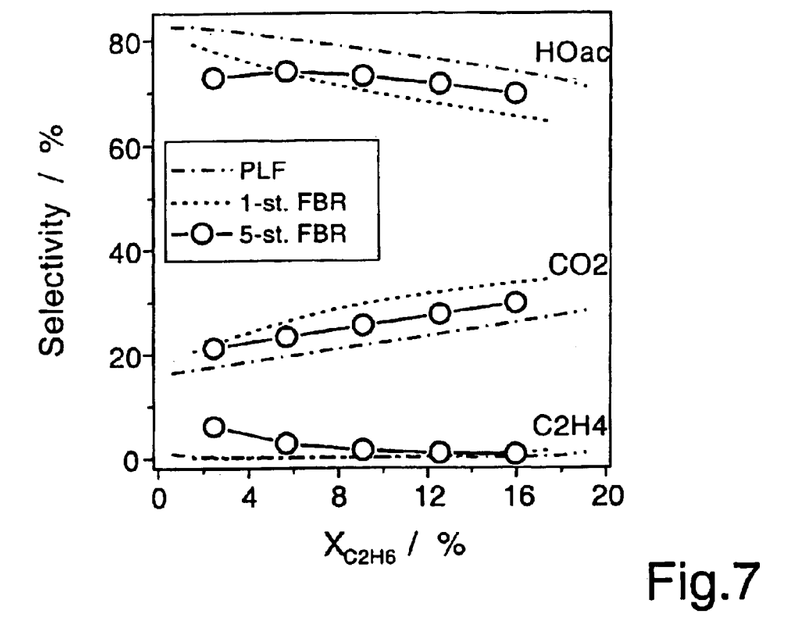
Figure 8:
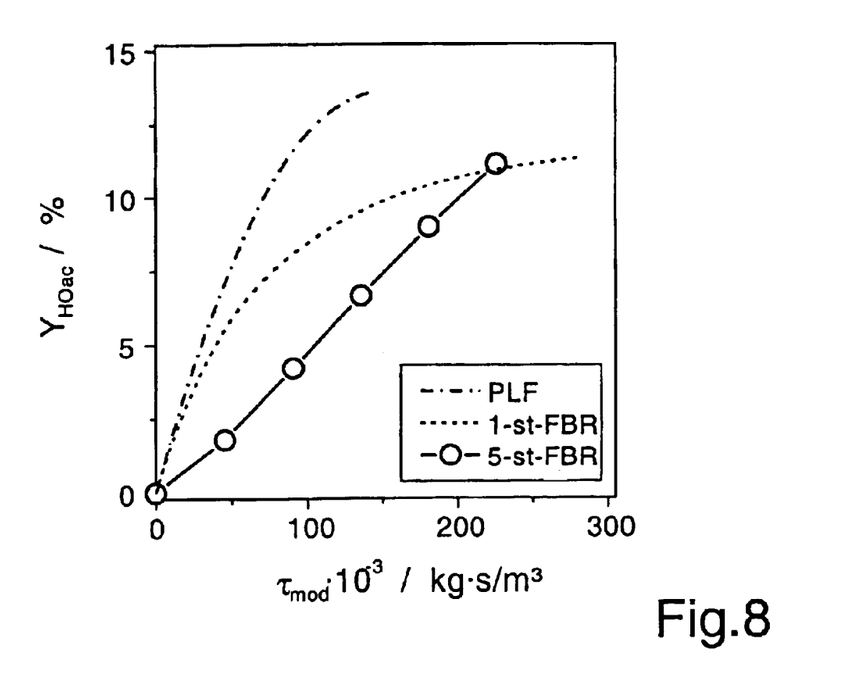

FIG. 7 shows the conversion selectivity curves and FIG. 8 the yield of acetic acid as a function of the residence time for a fixed bed, single-stage fluidized bed and 5-stage fluidized bed with divided introduction of oxygen; the points indicate the composition at the outlet of each stage (reaction conditions: T=260° C., $P_{tot}$=16 bar, $d_p$=60 $\mu$m, feed composition $C_2H_6$:$O_2$:$H_2O$:$N_2$=40:16:20:32 (in the case of divided introduction of oxygen in the first stage: 40:3.2:20:32)).

EXAMPLES

The present calculations were carried out under the assumption of a reactor diameter $D_i$ of 4 m, a particle size of 60 $\mu$m or 80 $\mu$m (according to the Geldart classification A), a density of the particles of 3100 kg/m$^3$ and a porosity of the fluidized reactor bed of 0.5 at the minimum fluidization velocity. The corresponding minimum fluidization velocity was 3.3 m/s (60 $\mu$m) or 5.85 m/s (at 80 $\mu$m). To achieve comparable fluid-dynamic conditions in the reactor in the simulation, the fluidized bed index $u/u_{mf}$ in the reactor was kept constant at 8.0 for all simulation conditions (different temperature, different composition of the gas stream fed in) by adjusting the gas velocity at the reactor inlet accordingly in the range from 4.67 m³/s to 5.40 m³/s. As gas distributor, a nozzle plate distributor having 800 orifices per m² was assumed.

In the calculation for the multistage fluidized-bed reactor without divided introduction of oxygen, each stage was modeled as an individual fluidized-bed reactor with its own gas distributor. In the case of a multistage fluidized bed with divided introduction of oxygen, the same flow of oxygen is added to the gas stream before each stage. The volume flow thus increases from stage to stage, so that the fluidized bed index increases slightly from 7.5 to 8.5. The volume flow was chosen so that the fluidized bed index $u/u_{mf}$ in the middle stage of the fluidized bed is 8.

In the figures, the simulation results for an ideal isothermal fixed-bed reactor under the same conditions are given for comparison (abbreviation: PLF). The modified residence time $\tau_{mod}$ specified in the figures and in the appendix is defined as the mass of catalyst divided by the volume flow at the reactor inlet under the given reaction conditions.

Example 1

Influence of the Particle Size

Simulation calculations were carried out for two different particle diameters, viz. 60 μm and 80 μm. In the case of the 60 μm particles, smaller bubbles having a maximum diameter of 4 cm were formed, while in the case of the 80 μm particles, bubbles having a diameter of up to 12 cm are formed.

The effect of better mass transfer and reduced backmixing in the case of small bubbles on the selectivities and the yield of acetic acid are shown in FIGS. 3 and 4. In addition, FIGS. 3 and 4 show that at a bubble diameter of $d_B$=1 cm, the achievable yields become the same as those in the fixed-bed reactor.

Furthermore, the results show that at constant conversion, the selectivity to acetic acid increases with decreasing bubble sizes. In addition, when the particle diameter becomes smaller, the yield of acetic acid $Y_{HOac}$ and also the space-time yield increase (FIG. 4).

The example shows that at a maximum bubble size $d_B$ of 1 cm, virtually identical results in respect of the selectivity to acetic acid and the space-time yield are obtained in the fluidized-bed reactor and the fixed-bed reactor, since at this bubble size virtually no inhibition of mass transfer between bubbles and emulsion phase occurs and, in addition, backmixing is reduced.

It can thus be shown that the low selectivity and space-time yield is at least partly attributable to undesirable backmixing in the fluidized bed and to slow mass transfer between the bubble phase and emulsion phase which leads to oxygen from the bubbles only slowly getting into the emulsion phase. In addition, a high oxygen concentration in the bubbles leads to increased carbon dioxide formation as a result of unselective further oxidation of the acetic acid and thus to a reduction in the acetic acid selectivity.

Example 2

Multistage Fluidized-bed Reactor

An additional possible way of reducing the undesirable backmixing in the fluidized bed is, apart from a reduction in the particle size, the use of a multistage fluidized-bed reactor. As a result of the gas distributors at the beginning of each stage, the average bubble size over the fluidized-bed reactor is smaller than in a single-stage fluidized bed, since bubble growth starts afresh in each stage.

FIGS. 5 and 6 show the results for various multistage fluidized-bed reactors:

"3St"—3-stage fluidized-bed reactor with 20 t of catalyst/ stage, height of the fluidized bed per stage=1.04 m "5St"—5-stage fluidized-bed reactor with 10 t of catalyst/ stage, height of the fluidized bed per stage=0.53 m "5St,vert"—5-stage fluidized-bed reactor with divided introduction of oxygen and 15 t of catalyst/stage, height of the fluidized bed per stage=0.78 m For comparison, the results for the single-stage fluidized-bed reactor (BAM) and the ideal fixed-bed reactor (PLF) are also shown in FIGS. 5 and 6.

At low ethane conversions, ethylene is formed with significantly higher selectivity in the 5-stage fluidized bed with divided introduction of oxygen than in the other fluidized bed reactors. This is attributable to the low oxygen concentration. In contrast, at higher ethane conversions, the differences in the selectivities between the various fluidized-bed reactors are low, (<2%). The highest acetic acid selectivity after the fixed-bed reactor of $S_{HOac}$=72.2% is obtained in the 5-stage fluidized bed with divided introduction of oxygen (at $X_{C2H6}$=8.6%). At the same ethane conversion, the selectivity in the fixed-bed reactor is $S_{HOac}$=77.5%.

The results in FIG. 5 show that use of a multistage fluidized bed enables the space-time yield to be increased significantly compared to a singe-stage fluidized bed. On the other hand, the divided introduction of oxygen leads to a reduction in the space-time yield, since the lower oxygen partial pressure reduces the reaction rate compared to the other reactors.

The simulation of the 5-stage fluidized-bed reactor with divided introduction of oxygen was repeated for a higher oxygen concentration which allows a higher ethane conversion and thus a higher acetic acid yield. Owing to the higher oxygen partial pressure, the reaction rate is increased. As before, the catalyst mass is 15 t/stage. The results of the simulation are shown in FIGS. 7 and 8.

In contrast to the results obtained with the low oxygen concentration (FIGS. 5 and 6), the conversion-selectivity curves in FIGS. 7 and 8 show more significant differences between the single-stage fluidized-bed reactor and the 5-stage fluidized-bed reactor. As a result of the divided introduction of oxygen, a significantly higher selectivity to acetic acid compared to the single-stage fluidized-bed reactor is obtained at the same ethane conversion (at $X_{C2H6}$= 16%: $S_{HOac,1-st}$=65.4% or $S_{HOac,5-st}$=69.7%). The loss of selectivity in the fluidized bed compared to the fixed bed is relatively small ($S_{HOac,PLF}$=73.6%). As before, the space-time yield obtained with divided introduction of oxygen is reduced compared to the fixed-bed reactor; however, it is at the level of the single-stage fluidized-bed reactor.

The following tables show the data for all figures.

TABLE 1

Conversion and selectivity data for the influence of the bubble size and the particle diameter (FIG. 3 and FIG. 4)

| $\tau_m$/kg · s · m⁻³ | $X_{C2H6}$/% | $X_{O2}$/% | $S_{C2H4}$/% | $S_{HOac}$/% | $S_{CO2}$/% |
|---|---|---|---|---|---|
| Particle diameter = 60 μm | | | | | |
| 7 540 | 1.19 | 11.19 | 0.28 | 80.33 | 19.39 |
| 15 080 | 2.22 | 21.29 | 0.22 | 78.80 | 20.99 |

TABLE 1-continued

Conversion and selectivity data for the influence of the
bubble size and the particle diameter (FIG. 3 and FIG. 4)

| $\tau_m$/kg·s·m$^{-3}$ | $X_{C2H6}$/% | $X_{O2}$/% | $S_{C2H4}$/% | $S_{HOac}$/% | $S_{CO2}$/% |
|---|---|---|---|---|---|
| 30 159 | 3.88 | 37.99 | 0.30 | 76.67 | 23.03 |
| 60 318 | 5.92 | 58.88 | 1.17 | 73.79 | 25.04 |
| 90 477 | 7.13 | 71.35 | 1.77 | 72.28 | 25.94 |
| 150 795 | 8.51 | 85.52 | 2.47 | 70.78 | 26.75 |
| 226 193 | 9.31 | 93.75 | 2.91 | 69.96 | 27.13 |
| 301 591 | 9.66 | 97.30 | 3.11 | 69.61 | 27.27 |
| Particle diameter = 80 μm | | | | | |
| 4 250 | 0.69 | 6.44 | 0.38 | 81.25 | 18.37 |
| 8 499 | 1.31 | 12.43 | 0.27 | 80.00 | 19.74 |
| 16 998 | 2.36 | 22.78 | 0.25 | 77.97 | 21.78 |
| 33 996 | 3.65 | 35.94 | 1.01 | 74.89 | 24.10 |
| 50 995 | 4.37 | 43.48 | 1.50 | 73.28 | 25.22 |
| 84 991 | 5.29 | 53.10 | 1.98 | 71.69 | 26.33 |
| 127 487 | 6.06 | 61.14 | 2.30 | 70.66 | 27.04 |
| 169 982 | 6.64 | 67.00 | 2.52 | 70.02 | 27.46 |
| 254 973 | 7.50 | 76.11 | 2.81 | 69.24 | 27.95 |
| Bubble diameter limited, $d_B$ = 1 cm | | | | | |
| 4 250 | 0.72 | 6.59 | 0.69 | 81.99 | 17.32 |
| 8 499 | 1.41 | 13.06 | 0.46 | 81.75 | 17.79 |
| 16 998 | 2.73 | 25.55 | 0.27 | 81.12 | 18.60 |
| 33 996 | 5.11 | 48.46 | 0.19 | 79.80 | 20.01 |
| 50 995 | 7.07 | 67.91 | 0.26 | 78.55 | 21.19 |
| 84 991 | 9.40 | 91.07 | 1.72 | 75.55 | 22.74 |
| 127 487 | 10.16 | 98.61 | 2.57 | 74.10 | 23.33 |
| For comparison: Plug-Flow-Reactor | | | | | |
| 1 700 | 0.28 | 2.48 | 2.52 | 81.21 | 16.27 |
| 4 250 | 0.72 | 6.54 | 0.98 | 82.48 | 16.54 |
| 8 499 | 1.42 | 12.98 | 0.51 | 82.53 | 16.96 |
| 16 998 | 2.78 | 25.74 | 0.27 | 81.93 | 17.79 |
| 33 996 | 5.23 | 49.22 | 0.18 | 80.52 | 19.30 |
| 50 995 | 7.24 | 69.06 | 0.26 | 79.19 | 20.55 |
| 67 993 | 8.75 | 84.07 | 0.93 | 77.52 | 21.55 |
| 84 991 | 9.63 | 92.70 | 1.82 | 75.97 | 22.22 |
| 127 487 | 10.28 | 99.18 | 2.58 | 74.65 | 22.76 |

TABLE 2

Multistage fluidized-bed reactors without side streams (all oxygen
is introduced into the first stage)
(FIG. 5 and FIG. 6)

| | $\tau_m$/kg·s·m$^{-3}$ | $X_{C2H6}$/% | $X_{O2}$/% | $S_{C2H4}$/% | $S_{HOac}$/% | $S_{CO2}$/% |
|---|---|---|---|---|---|---|
| 3-stage fluidized-bed reactor | | | | | | |
| Stage 1 | 60 318 | 5.91 | 58.88 | 1.17 | 73.79 | 25.04 |
| Stage 2 | 120 636 | 8.55 | 85.61 | 2.09 | 71.86 | 26.06 |
| Stage 3 | 180 954 | 9.49 | 95.22 | 2.71 | 70.82 | 26.48 |
| 5-stage fluidized-bed reactor | | | | | | |
| Stage 1 | 30 159 | 3.88 | 37.98 | 0.30 | 76.67 | 23.03 |
| Stage 2 | 60 318 | 6.56 | 65.11 | 0.88 | 74.90 | 24.22 |
| Stage 3 | 90 477 | 8.23 | 81.65 | 1.59 | 73.42 | 24.99 |
| Stage 4 | 120 636 | 9.14 | 90.64 | 2.20 | 72.36 | 25.44 |
| Stage 5 | 150 795 | 9.62 | 95.30 | 2.57 | 71.73 | 25.69 |

TABLE 3

Multistage fluidized-bed reactor with divided introduction of
oxygen (the oxygen conversion $X_{O2}$ is calculated per stage)
(FIG. 5 and FIG. 6)

| | $\tau_m$/kg·s·m$^{-3}$ | $X_{C2H6}$/% | $X_{O2}$/% | $S_{C2H4}$/% | $S_{HOac}$/% | $S_{CO2}$/% |
|---|---|---|---|---|---|---|
| low oxygen concentration | | | | | | |
| Stage 1 | 45 239 | 1.33 | 59.38 | 13.49 | 66.45 | 20.06 |
| Stage 2 | 90 477 | 3.02 | 57.95 | 7.90 | 70.64 | 21.45 |
| Stage 3 | 135 716 | 4.88 | 57.39 | 5.13 | 72.16 | 22.71 |
| Stage 4 | 180 954 | 6.73 | 57.06 | 3.62 | 72.48 | 23.90 |
| Stage 5 | 226 193 | 8.62 | 56.81 | 2.73 | 72.22 | 25.05 |
| increased oxygen concentration | | | | | | |
| Stage 1 | 45 239 | 2.47 | 58.47 | 5.99 | 72.77 | 21.24 |
| Stage 2 | 90 477 | 5.67 | 56.38 | 2.66 | 73.98 | 23.36 |
| Stage 3 | 135 716 | 9.10 | 55.10 | 1.42 | 73.09 | 25.49 |
| Stage 4 | 180 954 | 12.56 | 54.20 | 0.87 | 71.51 | 27.62 |
| Stage 5 | 226 193 | 15.96 | 53.49 | 0.60 | 69.69 | 29.72 |

TABLE 4

Conversion and selectivity data for the increased proportion of oxygen;
as a comparison with the 5-stage fluidized-bed reactor with divided
introduction of oxygen, the fixed-bed reactor and single-stage
fluidized-bed reactor are shown here.
(FIG. 7 and FIG. 8)

| $\tau_m$/kg·s·m$^{-3}$ | $X_{C2H6}$/% | $X_{O2}$/% | $S_{C2H4}$/% | $S_{HOac}$/% | $S_{CO2}$/% |
|---|---|---|---|---|---|
| single-stage fluidized-bed reactor | | | | | |
| 7 058 | 1.52 | 7.25 | 0.16 | 79.33 | 20.51 |
| 14 115 | 2.90 | 14.18 | 0.11 | 77.15 | 22.74 |
| 28 231 | 5.33 | 26.91 | 0.08 | 74.00 | 25.92 |
| 42 346 | 7.37 | 38.02 | 0.07 | 71.82 | 28.11 |
| 56 461 | 9.09 | 47.56 | 0.07 | 70.29 | 29.64 |
| 84 692 | 11.71 | 62.35 | 0.16 | 68.35 | 31.49 |
| 141 154 | 14.85 | 80.11 | 0.63 | 66.17 | 33.19 |
| 211 730 | 16.77 | 90.97 | 1.09 | 64.89 | 34.02 |
| 282 307 | 17.64 | 95.91 | 1.35 | 64.29 | 34.36 |
| Plug Flow Reactor | | | | | |
| 2 823 | 0.61 | 2.77 | 0.95 | 82.56 | 16.48 |
| 7 058 | 1.58 | 7.27 | 0.37 | 82.56 | 17.07 |
| 14 115 | 3.10 | 14.43 | 0.19 | 81.81 | 18.00 |
| 28 231 | 6.04 | 28.64 | 0.10 | 80.10 | 19.80 |
| 56 461 | 11.18 | 54.78 | 0.06 | 76.94 | 23.01 |
| 84 692 | 15.22 | 76.56 | 0.06 | 74.36 | 25.58 |
| 112 923 | 18.00 | 92.00 | 0.32 | 72.28 | 27.39 |
| 141 154 | 19.11 | 98.18 | 0.95 | 70.86 | 28.19 |

What is claimed is:

1. A process for preparing acetic acid comprising oxidizing ethane with molecular oxygen in a fluidized bed of catalyst particles, wherein the particle diameter of at least 70% of the catalyst particles used is less than or equal to 80 μm, the density of the catalyst particles used in the fluidized-bed reactor is from 500 kg/m$^3$ to 6,000 kg/m$^3$, the fluidized bed index is greater than or equal to 1 and the gas volume flow is selected so that the bubble diameter of the reaction gas mixture fed in in the fluidized-bed reactor is less than 12 cm.

2. A process as claimed in claim 1, wherein the gas volume flow is set so that the bubble diameter of the reaction gas mixture fed in is less than 5 cm.

3. A process as claimed in claim 1 wherein the particle diameter of from 10% to 60% of the catalyst particles is less than 60 μm.

4. A process as claimed in claim 1 wherein from 20 to 50% of the particles have a diameter of less than 40 μm.

5. A process as claimed in claim 1 wherein the catalyst particles are within a particle diameter range from 10 μm to 40 μm.

6. A process as claimed in claim 1 wherein the fluidized bed index is in the range of from 1 to 10.

7. A process as claimed in claim 1 wherein the catalyst used has the formula (I), $$Mo_a Pd_b X_c Y_d \qquad (I)$$

wherein

X is at least one element selected from the group consisting of Cr, Mn, Nb, Ta, B, Ti, V, Te, Re and W, Y is at least one element selected from the group consisting of B, Al, Ga, In, Pt, Zn, Cd, Bi, Ce, Co, Rh, Ir, Cu, Ag, Au, Fe, Ru, Cs, Mg, Ca, Sr, Ba, Li, K, Na, Rb, Be, Nb, Zr, Hf, Ni, P, Pb, Sb, Si, Sn, Tl and U and the indices a, b, c and d are the gram atom ratios of the corresponding elements, where, based on a=1, b is from 0.0001 to 0.01, c is from 0.1 to 1 and d is from 0 to 1, where X and/or Y may represent a plurality of elements.

8. A process as claimed in claim 1 wherein the catalyst is selected from the group consisting of $Mo_{1.0}Pd_{0.0005}V_{0.25}NB_{0.12}$, $Mo_{1.00}Pd_{0.0005}V_{0.45}Nb_{0.03}Sb_{0.01}Ca_{0.01}$, $Mo_{1.00}Pd_{0.0005}V_{0.45}Nb_{0.03}Sb_{0.01}Ca_{0.01}K_{0.015}$, $Mo_{1.00}Pd_{0.00075}V_{0.45}Nb_{0.03}Sb_{0.01}\ Ca_{0.01}$, $Mo_{1.00}Pd_{0.00075}V_{0.55}Nb_{0.03}Sb_{0.01}Ca_{0.01}$, $Mo_{1.00}Pd_{0.00075}V_{0.04}Nb_{0.06}Sb_{0.01}Ca_{0.01}$, $Mo_{1.00}Pd_{0.0008}V_{0.55}Nb_{0.06}Sb_{0.01}Ca_{0.01}$, $Mo_{1.00}Pd_{0.00085}V_{0.55}Nb_{0.06}Sb_{0.01}Ca_{0.01}$, $Mo_{1.00}Pd_{0.00075}V_{0.55}Nb_{0.09}Sb_{0.01}Ca_{0.01}$, $Mo_{1.00}Pd_{0.0008}V_{0.50}Nb_{0.15}Te_{0.01}Ca_{0.01}$ and $Mo_{1.00}Pd_{0.00075}V_{0.50}Nb_{0.09}W_{0.01}Pd_{0.0003}$.

9. A process as claimed in claim 1 wherein the reaction is carried out at a temperature from 100 to 500° C.

10. A process as claimed in claim 1 wherein the reaction is carried out at a reactor pressure in the range from 1 to 50 bar.

11. A process as claimed in claim 1 wherein not only ethane and molecular oxygen but also an inert gas, carbon dioxide and/or water vapor are present in the reaction gas mixture.

12. A process as claimed in claim 1 wherein the fluidized-bed reactor has a plurality of reaction stages or reaction zones.

13. A process as claimed in claim 12 wherein one or more reactants or water are fed into various zones or stages of a single-stage or multistage reactor.

* * * * *